US 7,585,281 B2

Sep. 8, 2009

(12) United States Patent
Nezhat et al.

(10) Patent No.: US 7,585,281 B2
(45) Date of Patent: Sep. 8, 2009

(54) VACUUM-ACTUATED TISSUE PERFORATION DEVICE FOR ESTABLISHING PNEUMOPERITONEUM

(75) Inventors: Camran Nezhat, Palo Alto, CA (US); Catherine Mohr, Mountain View, CA (US)

(73) Assignee: Aragon Surgical, Inc., Palo Alto, CA (US)

( * ) Notice: Subject to any disclaimer, the term of this patent is extended or adjusted under 35 U.S.C. 154(b) by 534 days.

(21) Appl. No.: 10/238,113

(22) Filed: Sep. 10, 2002

(65) Prior Publication Data

US 2004/0049127 A1    Mar. 11, 2004

(51) Int. Cl.
*A61B 10/00*   (2006.01)
*A61B 17/14*   (2006.01)
*A61B 17/32*   (2006.01)
*A61B 17/34*   (2006.01)
*A61M 37/00*   (2006.01)
*A61M 5/00*    (2006.01)
*A61M 5/32*    (2006.01)

(52) U.S. Cl. .................. 600/564; 600/562; 600/565; 600/566; 600/567; 604/115; 604/176; 604/23; 604/26; 606/184; 606/185

(58) Field of Classification Search ............. 600/560, 600/562, 564–567; 604/115, 176, 23, 26; 606/184, 185
See application file for complete search history.

(56) References Cited

U.S. PATENT DOCUMENTS

| | | | | |
|---|---|---|---|---|
| 2,743,723 A | * | 5/1956 | Hein | .......................... 604/115 |
| 3,263,683 A | * | 8/1966 | Uddenberg | .................. 604/317 |
| 4,299,219 A | * | 11/1981 | Norris, Jr. | .................... 604/115 |
| 4,633,865 A | * | 1/1987 | Hengstberger et al. | ...... 606/201 |
| 5,334,150 A | * | 8/1994 | Kaali | ..................... 604/164.08 |
| 5,354,307 A | * | 10/1994 | Porowski et al. | ............. 606/171 |
| 5,407,427 A | * | 4/1995 | Zhu et al. | ...................... 604/26 |
| 5,454,367 A | | 10/1995 | Moll et al. | |
| 5,465,711 A | | 11/1995 | Moll et al. | |
| 5,505,689 A | | 4/1996 | Kramer et al. | |
| 5,514,075 A | | 5/1996 | Moll et al. | |
| 5,515,283 A | | 5/1996 | Desai et al. | |
| 5,522,790 A | | 6/1996 | Moll et al. | |
| 5,527,264 A | | 6/1996 | Moll et al. | |
| 5,531,856 A | | 7/1996 | Moll et al. | |
| 5,545,123 A | | 8/1996 | Ortiz et al. | |
| 5,562,603 A | | 10/1996 | Moll et al. | |
| 5,569,165 A | | 10/1996 | Chin et al. | |
| 5,575,759 A | | 11/1996 | Moll et al. | |
| 5,669,883 A | | 9/1997 | Scarfone et al. | |
| 5,690,607 A | | 11/1997 | Chin et al. | |
| 5,871,471 A | * | 2/1999 | Ryan et al. | ............. 604/167.03 |
| 5,893,368 A | | 4/1999 | Sugerman | |

(Continued)

FOREIGN PATENT DOCUMENTS

GB    1180932    *    2/1970

*Primary Examiner*—Max Hindenburg
*Assistant Examiner*—Jeffrey G Hoekstra
(74) *Attorney, Agent, or Firm*—Michael A. Glenn; Glenn Patent Group

(57) ABSTRACT

A tissue perforation device and method. The device preferably includes a housing having a housing pass-through, a penetrator securely and sealably positioned so that the penetrator device passes through the housing pass-through, and a vacuum system comprising a vacuum source securely and sealably attached through the housing for advancing a patient's tissue onto the penetrator device.

8 Claims, 3 Drawing Sheets

U.S. PATENT DOCUMENTS

| | | |
|---|---|---|
| 6,042,539 A | 3/2000 | Harper et al. |
| 6,197,041 B1 | 3/2001 | Shichman et al. |
| 6,340,358 B1 | 1/2002 | Bohannon et al. |
| 6,899,106 B1 * | 5/2005 | Al-Killidar ................. 128/898 |

* cited by examiner

VACUUM-ACTUATED TISSUE PERFORATION DEVICE FOR ESTABLISHING PNEUMOPERITONEUM

BACKGROUND OF THE INVENTION

1. Field of the Invention

The present invention relates to a tissue perforation device and method. More particularly, the present invention relates to a device, which draws skin and underlying tissue onto a perforation device and away from vulnerable underlying structures.

2. Background of the Invention

Significant morbidity and mortality occurs each year by iatrogenic injuries during establishment of pneumoperitoneum prior to laparoscopic surgical procedures. The main source of these injuries is inadvertent perforation of blood vessels or organ structures within the abdominal cavity when the penetration device (needle, trocar or punch biopsy cutting tool) is advanced too far through the abdominal wall piercing the underlying organs that are located adjacent thereto. These injuries are more common with inexperienced surgeons, but can occur even in the most experienced hands. Built-in safety devices exist in the perforation devices themselves, but injuries still occur because of the close proximity of the structures that are intended to be perforated and those to be avoided.

Vacuum has been used to fix or distort the body and body cavities. In addition, techniques exist for insufflation, or mechanical or vacuum elevation of the abdominal wall during surgical procedures.

In U.S. Pat. No. 6,042,539, a vacuum-actuated tissue-lifting device and method for performing a surgical procedure in an operative space of a patient are disclosed. The preferred device has a shell with a profile configured to surround a tissue surface of the patient, a vacuum port located on the shell for applying a vacuum between the shell and the tissue surface, and an air conduit extending through the shell to permit air to pass into the operative space of the patient when vacuum is applied.

In U.S. Pat. No. 6,340,358, a trocar is disclosed having a safety shield control mechanism that prevents the inner cannula from rotating and from moving axially when in the locked position. The safety shield control mechanism applies consistent pressure on the safety shield and has an open architecture for ease of sterilization. The trocar provides holding levels for different sizes of hands.

In U.S. Pat. No. 6,197,041, a pneumatically powered trocar assembly is disclosed that includes a source of compressed gas which releases a metered amount of gas to a chamber. A piston slidably positioned within the chamber is driven forward by the compressed gas introduced therein, and an obturator with a tissue piercing tip are advanced thereby. Optionally, a sensor detects the presence of body tissue within the cutting path of the tip and blocks the passage of compressed gas to the chamber, or alternatively, opens an escape vent to release compressed gas therefrom if insufficient body tissue resistance is encountered.

In U.S. Pat. No. 5,669,883, a Veress needle and cannula assembly is disclosed that includes a stainless steel cannula assembly with a cannula having an outer diameter of approximately 4 mm and a Veress needle assembly having a Veress needle with an outer diameter of approximately 3 mm. The cannula assembly includes a proximal valve assembly and the Veress needle is insertable through the valve assembly.

In U.S. Pat. No. 5,690,607, an apparatus is disclosed for allowing two retractors to be used to lift the abdominal wall to provide improved visualization and working space in the abdomen of obese patients, and in the lateral regions of the abdomen of normal patients. The apparatus connects a first retractor and a second retractor to a mechanical lifting arm, and comprises a bar, and first, second, and third connecting devices. The apparatus is used by making a first incision and a second incision in the abdominal wall at separated locations. The first retractor is inserted into the first incision, and the second retractor is inserted into the second incision. The first retractor and the second retractor are attached to the crossbar, anal a lifting force is applied to the crossbar.

In U.S. Pat. No. 5,575,759, an apparatus for retracting an organ to gain access to treat a tissue is disclosed. The apparatus has a main envelope, a second envelope, a first inflation device and a second inflation device. The main envelope encloses a main chamber, and includes a window and a removable window. The second envelope covers substantially all the main envelope, except the window and the removable window. The second envelope and the main envelope enclose a second chamber outside the main chamber. The first inflation device passes a fluid into the main chamber to expand the main chamber and the second chamber from a compacted state to retract the organ. The second inflation device passes a fluid into the second chamber to further expand the second chamber to maintain the organ in its retracted state after fluid has been released from the main chamber.

In U.S. Pat. No. 5,562,603, an apparatus is described for laparoscopically retracting an organ inside the body to provide surgical access to adjacent tissue. The apparatus includes a thin, flexible envelope, which encloses a chamber. The envelope is laparoscopically insertable in a collapsed state into a body cavity, and the chamber is inflatable to an expanded state following introduction of the envelope into the body. Inflation of the chamber causes retraction of adjacent tissue. An elastomeric seal is insertable into the chamber following inflation and is attachable to part of the envelope inside the chamber following inflation of the chamber. The seal provides a gas-tight seal to maintain the chamber in the expanded state, and to maintain the organ in the retracted state, notwithstanding the piercing of an aperture in the part of the envelope covered by the seal.

In U.S. Pat. No. 5,531,856, an inflatable apparatus for organ retraction includes a main envelope that forms a main chamber is disclosed. An additional chamber is formed by attaching the periphery of an additional envelope to the outside or the inside of the main envelope. The part of the surface of the main envelope that is not covered by the additional envelope provides a plurality of windows, which, after the additional chamber is inflated, may be at least partially removed to provide apertures through, which treatment or observation can be carried out.

In U.S. Pat. No. 5,522,790, a first inflatable retraction device is disclosed having a first inflatable chamber and a non-pressurized chamber inside the main chamber. The non-pressurized chamber is expanded by inflating a second inflatable chamber. The non-pressurized chamber enables the main chamber to remain inflated when an aperture is cut in the envelope of the main chamber, through which treatment is carried out. A second inflatable retraction device has an inflatable retractor and a maintainer. The inflatable retractor retracts the organ and the maintainer maintains the organ in its retracted condition after the inflatable retractor is deflated. The maintainer can be inflatable, and can be inside or outside the inflatable retractor. A self-retracting endoscope has an optical assembly with an expandable retractor fitted to its distal end. The distal end of the endoscope is inserted into the body with the retractor in a collapsed condition. The retractor is then expanded to retract organs that would otherwise obstruct the view from the distal end of the optical assembly. After observations are complete, the retractor is returned to its collapsed condition. An insertion tube enables cylindrical objects, such as packaged inflatable retraction devices, to be pulled, instead of pushed, into the body. The additional chamber of an inflatable retraction device having two inflatable chambers is filled with a slurry of a particulate solid in a liquid. The liquid is removed and the additional chamber evacuated to consolidate the particulate solid. This increases the retracting strength of the additional chamber.

In U.S. Pat. No. 5,505,689, a fan retractor is disclosed for laparoscopic surgery has a pair of angle-shaped elements with first legs disposed in parallel relationship to one another and second legs extending laterally from the first legs for movement between a juxtaposed collapsed condition and a fanned-out expanded condition responsive to rotation of the first legs about their longitudinal axes. Actuators are provided on the first legs to move the second legs between the collapsed and extended conditions. A first lock engages the actuators to lock the second legs in the extended condition and against movement toward or away from one another. A second lock in the form of a block slidably received on the first legs is selectively engageable between the second legs when in the extended condition. When engaged, the second lock serves both to block the second legs from movement toward one another and to restrain the first legs against movement away from one another.

In U.S. Pat. No. 5,465,711, an organ or tissue plane to be retracted is performed to gain access for a surgical instrument to treat an organ or tissue plane to be treated. An inflatable retractor, including a main envelope enclosing a main chamber, is provided with the main envelope in a collapsed state. The main envelope of the retractor is placed adjacent the organ or tissue plane to be retracted. The main chamber is inflated to an expanded state to retract the organ or tissue plane to be retracted. An aperture is pierced in the main envelope to provide access for the surgical instrument passed into the main chamber to contact an organ or tissue plane to be treated while the main chamber is maintained in the expanded state, notwithstanding the aperture pierced in the main envelope.

In U.S. Pat. No. 5,454,367, an inflatable retractor including a main envelope enclosing a main chamber is provided. The main envelope is provided in a collapsed state. An elastomeric window is also provided. The main envelope of the inflatable retractor is placed adjacent the organ inside the body, and the main chamber is expanded to an expanded state to retract the organ. Following inflation of the main chamber to the expanded state, the elastomeric window is attached to the main envelope inside the main chamber to cover part of the main envelope. The surgical instrument is passed into the main chamber. An aperture is pierced in the pan of the main envelope covered by the elastomeric window to provide access for the surgical instrument to contact the tissue. The elastomeric window provides a gas-tight seal to maintain the main chamber in the expanded state.

In contrast to known techniques and methods, the preferred device of the present invention advances tissue to be perforated onto a stationary perforation device and away from the underlying structures. The simplicity of technique leads to a short learning curve and virtually eliminates the possibility of iatrogenic injuries.

SUMMARY OF THE INVENTION

The preferred embodiment of the invention advances tissue to be perforated onto a perforation device or piercing instrument. Presently, the primary intended use of the preferred embodiment is for pulling the abdominal wall onto a perforation device, such as a Veress needle, trocar or punch biopsy cutting tool, and away from abdominal viscera and great vessels for the initial establishment of pneumoperitoneum. Another intended application for the preferred embodiment is for implanting a device below the skin surface for diagnostic or therapeutic purposes. The present invention is not limited to these applications and may be extended into other diagnostic and therapeutic applications.

The limitations imposed on the invention are expressly set out in the appended claims only. The invention itself, however, both as to its construction and its method of operation, together with additional objects and advantages thereof, will be best understood from the following description of the specific embodiments when read and understood in connection with the accompanying drawings.

10—tissue perforation and inflation device (10)
12—housing(12)
12A—housing seal (12A)
12C—housing pass-through (12C)
14—penetrator device (14)
14A—penetrator device tip (14A)
14B—penetrator device valve (14B)
14C—hollow shaft of penetrator device (14C)
16—vacuum system (16)
16A—vacuum attachment tube (16A)
16B—vacuum valve (16B)
18—abdominal wall (18)
18A—abdominal wall bubble (18A)
20—top center housing (20)
22—O-ring (22)
24—optical device or camera (24)
30—"clamshell" housing (30)
32—collar or adapter plate (32)
34—left half section (34) of housing (30)
36—right half section (36) of housing (30)
38—left sealing edge (38)
40—right sealing edge (40)
42—left half seal (42)
44—right half seal (44)
50—bell housing (50)
52—opening (52)
54—bell housing pass-through (54)

DETAILED DESCRIPTION OF THE PREFERRED EMBODIMENT

The following is a detailed description of the preferred embodiment of the invention.

Figure 1:
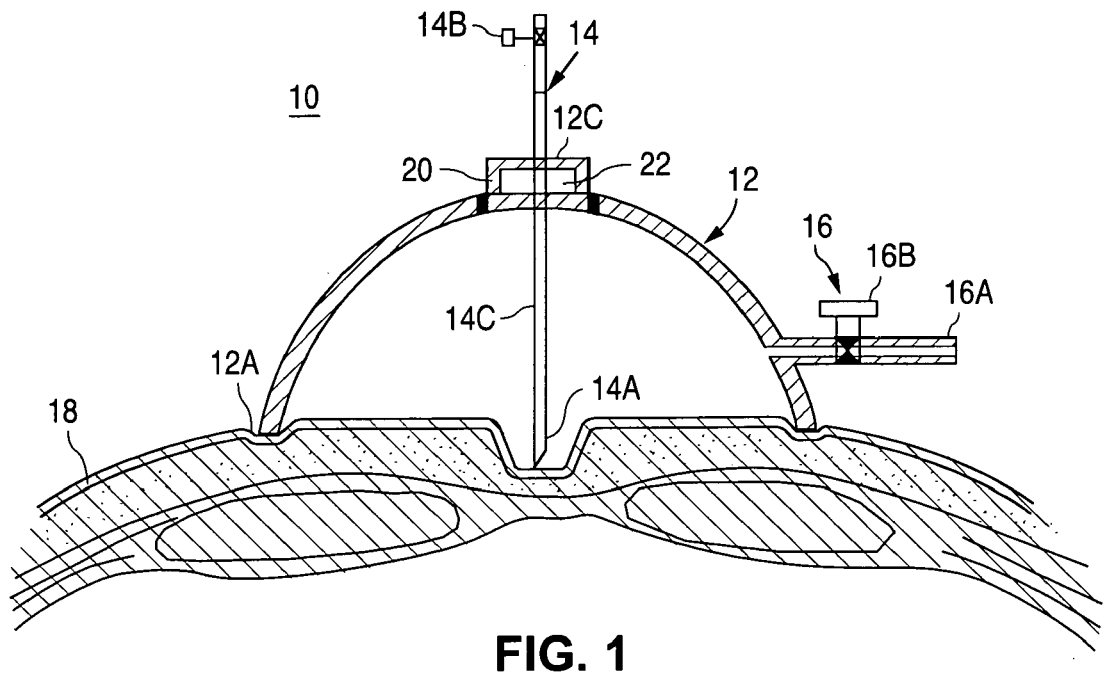
FIG. 1 is a side view of a tissue perforation device (10) positioned over a non-extended abdominal wall (18).
Figure 2:
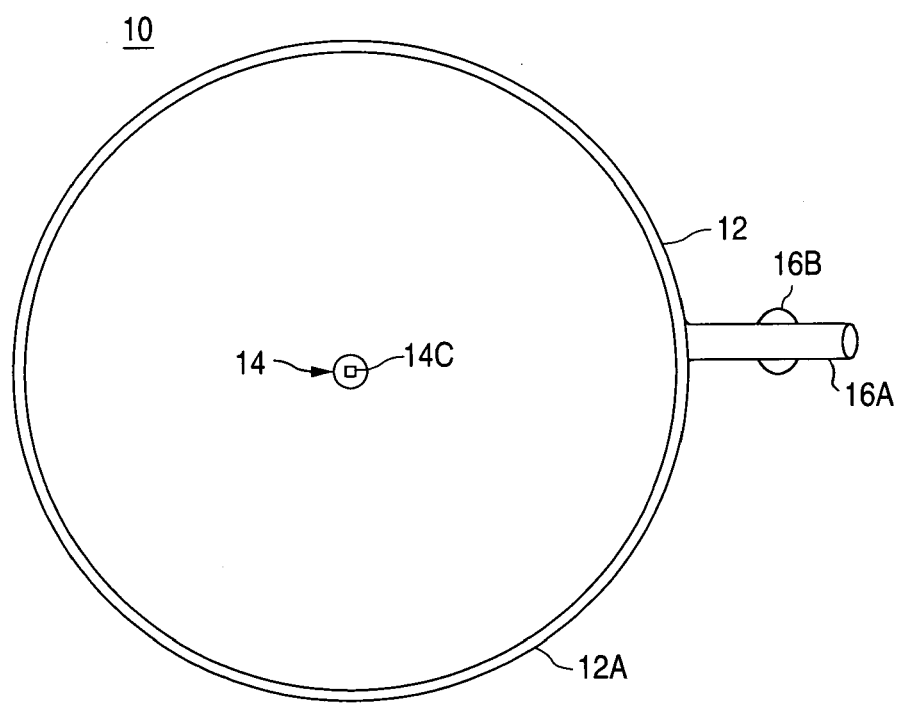
FIG. 2 is a bottom view of the perforation device (10).

Referring to FIG. 1 and FIG. 2, which are a side and bottom view, respectively, of a perforation device (10) positioned over a non-extended abdominal wall (18). The device (10) comprises a housing (12) having a housing pass-through (12C) and a housing seal (12A) along a perimeter functioning to form a tight seal between the housing (12) and an abdominal wall (18). The housing (12) is manufactured from a strong non-collapsible material to withstand the internal negative pressure in the range of about 50 to 250 mm Hg exerted therein. Suitable materials are specifically designed for medical use and capable of sterilization. The materials include plastic, plastic composite, rubber, rubber composite, fiberglass, epoxy, glass, glass composite, and the like. Plastic, such as polycarbonate, and plastic composites are particularly well suited due to its superior strength, transparency, rapid manufacturing and low cost. The housing (12) is usually translucent or transparent. Transparency is preferable to allow the physician to monitor the perforation. Housing (12) is sized to accommodate adults and children of different sizes and/or body mass indexes. The diameter of the circumference of housing (12) in contact with the abdomen for adults ranges from about 3 inches to 8 inches and for pediatric patients from 1½ to 3 inches.

A penetrator device (14) can be securely and sealably positioned through a top center housing (20) of the housing (12). The seal and fixation of the penetrator device (14) can be done by means of the O ring (22). The seal and fixation of the penetrator device (14) can also be accomplished by other means, e.g., by pressing the operator's fingers on penetrator device (14) and braced against the housing pass-through (12C). The penetrator device (14) comprises a penetrator device tip (14A), such as a Veress needle, trocar, or other suitable device, designed to penetrate or cut tissue. The penetrator device (14) has a penetrator device valve (14B) for allowing the hollow shaft of the penetrator device (14C) either to introduce ambient room air, or for connection to a pressurized source of a gas, e.g., carbon dioxide, helium, nitrogen, air and mixtures thereof, for insufflation. The tissue perforation device (10) further comprises a standard operating room vacuum system (16). A vacuum tube (16A) is securely and sealably attached to the housing (12) through a valve or pressure regulator (16B), which functions to regulate the amount of negative pressure exerted within the housing (12).

Figure 3:
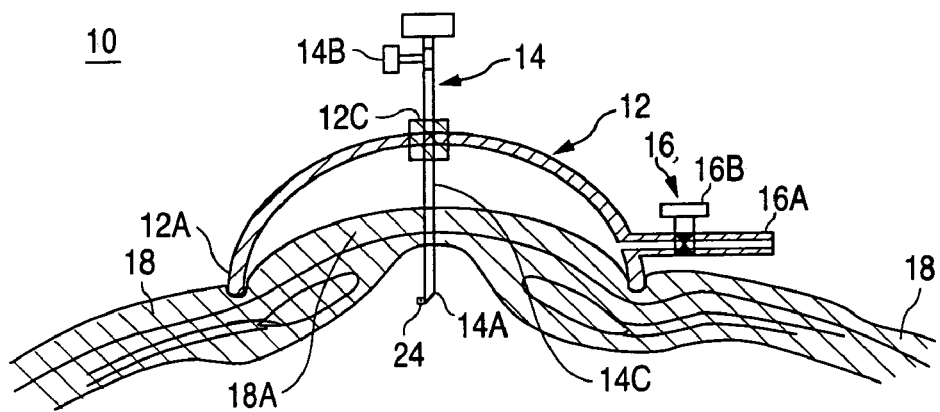
FIG. 3 is a side view of the perforation device (10) exhibiting an extended abdominal wall (18) forming an abdominal wall bubble (18A).

Referring now to FIG. 3, an extended abdominal wall (18) is shown with an abdominal wall bubble (18A). In the preferred embodiment, abdominal wall bubble (18A) is formed by applying negative pressure at vacuum attachment tube (16A), which extends into and is sealed against housing (12). Internal negative pressure within the housing (12) creates an abdominal wall bubble (18A) within the housing (12) and elevates the abdominal wall (18) away from the underlying organs and vascular structures. As the abdominal wall bubble (18A) enlarges, the abdominal wall (18) is advanced onto the stationary penetrator device tip (14A). Room air or inert gas introduced through penetrator device valve (14B) into the peritoneal cavity further facilitates the separation between the abdominal wall (18) and the underlying organs and vessels. Preferably, the penetrator device (14) contains an optical device or integral camera (24) at its tip to direct visualization of the passage of penetrator device (14) through tissue.

The distance of tissue movement is controlled directly by the operator through regulation of the vacuum. This may be controlled by periodic opening of a vacuum valve, or through a regulator (16B). Optimal vacuum will be a function of the tissue characteristics, and will be regulated by the operator to achieve the desired tissue displacement.

Figure 4:
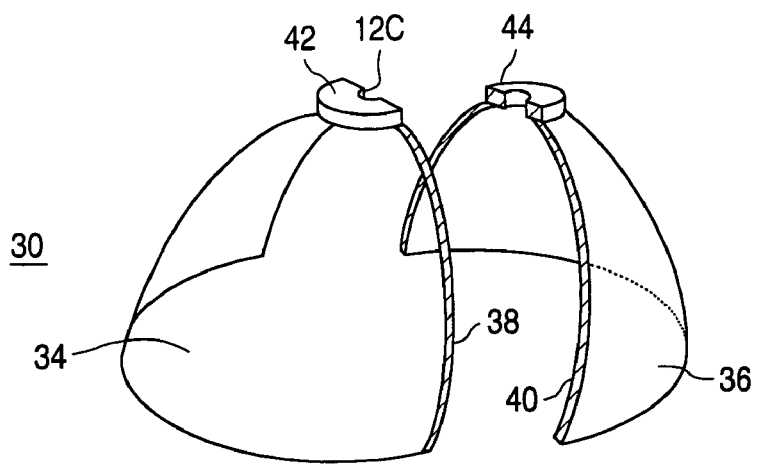
FIG. 4 is an exploded perspective view of a "clamshell" housing (30).
Figure 4A:
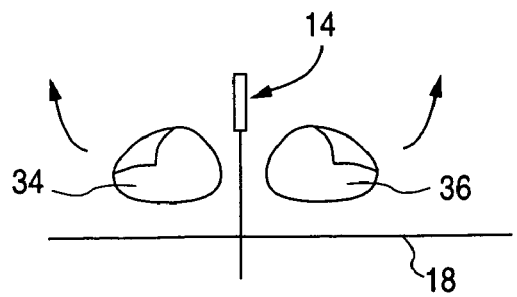
FIG. 4a is a view of the clamshell housing (30) being removed after penetration with penetrator device (14).
Figure 5:
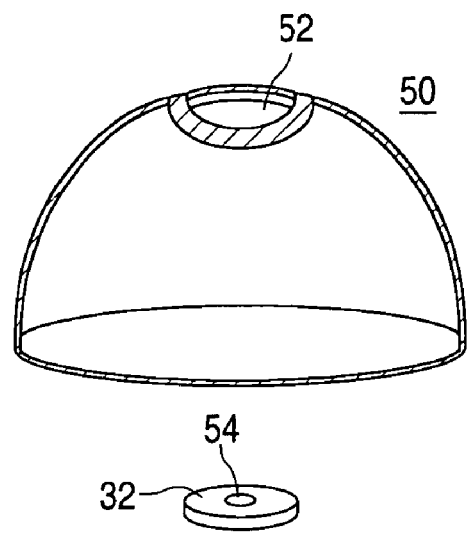
FIG. 5 is a side view of a bell housing (50).

Following penetration and insufflation, the applied vacuum may be released and the housing (12) removed by means of a "clamshell" housing (30) shown in FIGS. 4 and 4A or by means of an adaptor plate or collar (32) shown in FIG. 5 while leaving the penetrator device (14) in place through the abdominal wall (18).

Referring now to FIG. 3, an extended abdominal wall (18) is shown with an abdominal wall bubble (18A). In the preferred embodiment, abdominal wall bubble (18A) is formed by applying negative pressure at vacuum attachment tube (16A), which extends into and is sealed against housing (12). Internal negative pressure within the housing (12) creates an abdominal wall bubble (18A) within the housing (12) and elevates the abdominal wall (18) away from the underlying organs and vascular structures. As the abdominal wall bubble (18A) enlarges, the abdominal wall (18) is advanced onto the stationary penetrator device tip (14A). Room air or inert gas introduced through penetrator device valve (14B) into the peritoneal cavity further facilitates the separation between the abdominal wall (18) and the underlying organs and vessels. Preferably, the penetrator device (14) contains an optical device or integral camera (24) at its tip to direct visualization of the passage of penetrator device (14) through tissue.

FIG. 4A shows "clamshell" housing (30) being removed after the abdominal wall (18) has been penetrated with the penetrator device (14) and the vacuum has been released to leave penetrator device (14) in place without its disturbance.

Figure 5A:
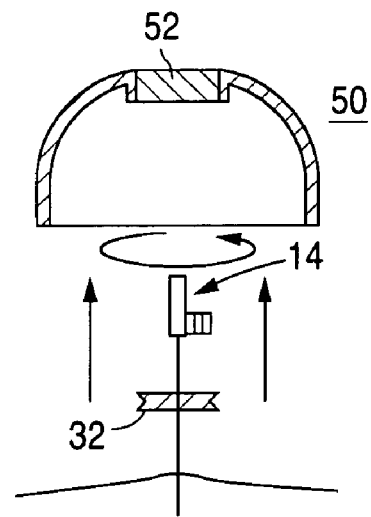
FIG. 5a is a perspective view of the bell housing (50) being removed after penetration with penetrator device (14).

FIG. 5 and 5A shows another alternative embodiment of housing (12). In this embodiment, a perspective view of a bell housing (50) having opening (52) to accommodate the adaptor plate or collar (32) is shown. In this embodiment, a needle or trocar is sealed within pass-through (54) in an adapter plate or collar (32), which is sealingly mounted in opening (52) of housing (50). Adapter plate (32) has a ¼ turn bayonet or thread on its edge. When the surgeon makes a ¼ (90 degrees) turn of the adapter plate (32) relative to the bell housing (50), adapter plate (32) is released from opening (52).

FIG. 5A shows the bell housing (50) being removed after the abdominal wall (18) has been penetrated with the penetrator device tip (14A), the vacuum has been released, and the penetrator device (14) has been rotated to leave both the adaptor plate (32) and penetrator device tip (14A) in place.

As this device may be adapted to work with any current or future commercially available trocar or Veress needle devices simply by changing the size of the pass-through (54) in the adaptor plate (32), the techniques for testing for adequate penetration past the peritoneum during establishment of pneumoperitoneum will be device dependant and are not described herein as they are well known to those skilled in the medical arts.

EXAMPLE

This example illustrates one embodiment of the present invention shown in FIGS. 1 and 3 in which housing (12) was a TUPPERWARE® bowl having O-ring (22) inserted in the center of the bottom of the bowl. The example is for illustrative purposes only and is not meant to limit the scope of the claims in any way.

In experimentation with a post mortem female pig, a standard hospital 300 mm Hg vacuum source was used to elevate the external abdominal surface 2-4 inches, depending on the amount of vacuum applied by vacuum system (16). The stationary Veress needle (14C) penetrated the pig's abdomen without difficulty and water was observed to drain upon penetration. $CO_2$ was attached and the abdomen insufflated to 12 mm Hg. Following insufflation, a 10 mm Ethicon Endo- Surgery trocar was installed at the midline 1" caudal to the xiphoid and a 30° Stortz camera (24) was inserted to verify uninjured tissue below the needle entry site, and to observe the inside abdominal wall. The experimental needle was removed and the experiment repeated at 2 mm Hg insufflation under direct observation from inside the abdomen. After external application of vacuum, from inside the abdomen, the abdominal wall could be seen arching up and away from the internal contents, and the needle tip was seen penetrating the displaced tissue.

It will be understood that each of the elements described above, or two or more together, may also find a useful application in other types of constructions differing from the type described above. An example of another application of the apparatus of the present invention is the performance of a surface skin biopsy where the stationary penetrator device (14) is designed to only penetrate a certain distance into tissue of the abdominal wall (18).

While the invention has been illustrated and described as embodied in an abdomen perforation and inflation device, it is not intended to be limited to the details shown, since it will be understood that various omissions, modifications, substitutions and changes in the forms and details of the device illustrated and in its operation can be made by those skilled in the art without departing in any way from the spirit of the present invention. What is claimed as new and desired to be protected by Letters Patent is set forth in the appended claims.

What is claimed is:

1. An apparatus for establishing pneumoperitoneum, comprising:
    a housing manufactured from strong non-collapsible material capable of withstanding an internal negative pressure of 50 to 250 mm Hg and having an opening for resting on an abdominal wall of a patient, a user adjustable vacuum valve, and a pass-through;
    an external vacuum system, said vacuum system exerting a negative pressure of 50-250 mm Hg in said housing;
    a first conduit for exerting negative pressure via said vacuum system, said first conduit comprising a vacuum tube coupled via said vacuum valve for exerting said negative pressure into said housing to form a tight seal between a housing seal and said abdominal wall of a patient;
    wherein an abdominal wall bubble is formed within the housing by exerting sufficient negative pressure with said vacuum system into said housing to elevate the abdominal wall away from underlying organs or vascular structure of the patient;
    a penetrator device that is adapted to be introduced into said housing via said pass-through;
    said penetrator device being adapted to pierce the abdominal wall, wherein said vacuum systems is adapted to continue to exert said negative pressure to advance the abdominal wall toward and into contact with the penetrator device;
    said vacuum system, upon said penetrator device contacting said abdominal wall, adapted to continue to exert said negative pressure to continue advancing said abdominal wall into said penetrator device, said penetrator device adapted to pierce and penetrate through said abdominal wall;
    said vacuum system adapted to form a peritoneal space by elevating said abdominal wall by exertion of said negative pressure into said housing and by a second conduit that is adapted to inject inert gas into said peritoneal space; and
    said second conduit adapted to increase separation between the abdominal wall and the underlying organs or vascular structure of the patient by injecting said inert gas into said peritoneal space between the abdominal wall and the organs or vascular structure that underlies the abdominal wall of the patient.

2. The apparatus for establishing pneumoperitoneum as described in claim 1, wherein the penetrator device comprises a tip that is selected from a group consisting of a needle and a trocar.

3. The apparatus for establishing pneumoperitoneum as described in claim 1, the penetrator device comprising a punch biopsy cutting tool.

4. The apparatus for establishing pneumoperitoneum as described in claim 1, wherein the penetrator device contains an optical device or integral camera at a tip thereof to allow direct visualization of the passage through tissue.

5. The apparatus for establishing pneumoperitoneum as described in claim 1, wherein the second conduit injects an inert gas that is selected from the group consisting of carbon dioxide, helium, nitrogen, and mixtures thereof.

6. The apparatus for establishing pneumoperitoneum as described in claim 1, further comprising:
    said housing being configured to be separable into two sections after penetration by the penetrator device and the release of the negative pressure and to be removable from the abdominal wall;
    wherein the penetrator device is adapted to be left in place through the abdominal wall.

7. The apparatus for establishing pneumoperitoneum as described in claim 1, wherein the housing comprises an opening for an adapter plate having a pass-through for the penetrator device that is removable from the abdominal wall after penetration by the penetrator device and the release of the negative pressure, and wherein the penetrator device is adapted to be left in place through the abdominal wall.

8. The apparatus for establishing pneumoperitoneum as described in claim 1, further comprising:
    a penetrator device valve for connection of said second conduit to a pressurized source of inert gas; and
    a pressure regulator for connection to said first conduit to regulate the amount of negative pressure exerted with said housing by said external vacuum system.

* * * * *